United States Patent [19]

Iwamoto et al.

[11] Patent Number: 4,758,644

[45] Date of Patent: Jul. 19, 1988

[54] BROMOSTYRENE COMPOSITION

[75] Inventors: Mune Iwamoto; Norifumi Ito; Kazuo Sugazaki; Tetsuyuki Matsubara; Toshihiko Ando, all of Kanagawa, Japan

[73] Assignee: Mitsui Toatsu Chemicals, Inc., Tokyo, Japan

[21] Appl. No.: 943,892

[22] Filed: Dec. 18, 1986

Related U.S. Application Data

[63] Continuation of Ser. No. 828,218, Feb. 10, 1986, abandoned.

[30] Foreign Application Priority Data

Feb. 19, 1985 [JP]  Japan ................................. 60-29443

[51] Int. Cl.$^4$ .......................... C08K 5/13; C08F 12/16
[52] U.S. Cl. ...................................... 526/293; 526/83; 526/84
[58] Field of Search ........................... 526/83, 84, 293

[56] References Cited

U.S. PATENT DOCUMENTS

| | | | |
|---|---|---|---|
| 3,225,108 | 12/1965 | Sturgis | 526/212 |
| 4,466,904 | 8/1984 | Watson | 252/402 |
| 4,468,343 | 8/1984 | Butler | 252/403 |
| 4,482,684 | 11/1984 | Gardner | 526/210 |
| 4,671,418 | 2/1986 | Younes | 525/148 |

Primary Examiner—Christopher Henderson
Attorney, Agent, or Firm—Jeffers, Hoffman & Niewyk

[57] ABSTRACT

A bromostyrene composition having overcome the unstability of bromostyrenes and being stable at the time of its storage and transportation is provided, which composition comprises 100 parts by weight of a styrene substituted with one, two or three bromine atoms on the benzene nucleus thereof or a mixture of the foregoing, 20 to 3,000 parts by weight of an aromatic vinyl compound such as styrene and 0.001 to 0.05 part by weight of a polymerization inhibitor.

4 Claims, No Drawings

BROMOSTYRENE COMPOSITION

BACKGROUND OF THE INVENTION

This is a continuation of application Ser. No. 828,218, filed Feb. 10, 1986, now abandoned.

This invention relates to a composition of mono-, di- or tribromostyrene or mixtures of the foregoing which is easy in storage and handling.

These bromostyrenes (hereinafter abbreviated to BS) are useful for obtaining a fire retardant polymer by copolymerizing them with another copolymerizable monomer such as styrene (e.g. see Japanese patent application laid-open No. Sho 55-23151/1980).

BS is very unstable and naturally polymerizes at room temperature (20° C.) and hence its handling is very difficult. Thus, in order to prevent such polymerization, it has so far been necessary to add a large quantity (about 0.1 part by weight based on 100 parts by weight of BS) of a polymerization inhibitor thereto or keep BS at an extremely low temperature of −20° C. or lower.

However, when a large quantity of a polymerization inhibitor is added, it is inevitable to remove the polymerization inhibitor by distillation or the like means in advance of polymerization, and if it is used without removing the inhibitor, a problem is raised that this has a bad influence upon the resulting polymer.

Further, when BS is unstabilized, even if it is stored at a low temperature, a natural polymerization occurs gradually so that an abnormal polymerization occurs due to its reaction heat and when it is handled in a large quantity, there is a fear that a run-away reaction may occur; hence a problem of maintenance has been raised.

Further, other problems have been raised that the polymer becomes a cause of clogging its transportation pipe, and a natural polymer mixes in the final polymer product to become a cause of degrading the physical properties of the polymer product.

SUMMARY OF THE INVENTION

The object of the present invention is to provide a BS composition having overcome the above unstability of BS and having stability at the time of its storage and transportation.

The present inventors have made extensive research in order to achieve the above object, and as a result, have found that surprisingly enough, when a specified quantity of an aromatic vinyl compound is added to BS, the stability of BS is notably improceed; thus the present invention has been attained.

The present invention resides in a bromostyrene composition comprising 100 parts by weight of a styrene substituted with one, two or three bromine atoms on the benzene nucleus thereof or a mixture of the foregoing, 20 to 3,000 parts by weight of an aromatic vinyl compound and 0.001 to 0.05 part by weight of a polymerization inhibitor.

DETAILED DESCRIPTION OF THE INVENTION

BS as the object of the present invention is a styrene substituted with one, two or three bromine atoms on the benzene nucleus thereof or mixtures of the foregoing.

The above-mentioned bromine-substituted styrenes will hereinafter be referred to as monobromostyrene, dibromostyrene and tribromostyrene. Examples of the mixtures of the bromostyrenes are those consisting of 5 to 10% by weight of monobromostyrene, 70 to 85% by weight of dibromostyrene and 5 to 15% by weight of tribromostyrene. In the present invention, when BS contains 10% by weight or more of dibromostyrene, a very good effectiveness is exhibited.

Examples of the aromatic vinyl compound used in the present invention are styrene, substituted styrenes such as α-methylstyrene, para-methylstyrene, para-tertiary-butylstyrene, vinylnaphthalene, etc. These compounds may be used in admixture.

The quantity of the aromatic vinyl compound used is 20 to 3,000 parts by weight, preferably 30 to 1,000 parts by weight, particularly preferably 40 to 400 parts by weight, based on 100 parts by weight of BS, and determined taking it into consideration to subject the composition of the present invention to polymerization reaction. If the quantity is less than 20 parts by weight, almost no effectiveness of stabilizing BS is exhibited, while if it exceeds 3,000 parts by weight, BS concentration at the time of polymerization is so low that it is impossible to directly use the resulting composition as the raw material for producing fire retardant polymers, that is, use of such less or larger quantity is not practical.

As to the polymerization inhibitor used in the present invention, any of compounds which are usually used as polymerization inhibitor for styrene may be used, and examples thereof are polymerization inhibitors of cresols, catechols, quinones, amines, etc., and preferably para-tertiary-butylcatechol (PTBC), hydroquinone (HQ), hydroquinone monomethyl ether (MQ), etc.

The quantity of the polymerization inhibitor used in 0.001 to 0.05 part by weight, preferably 0.002 to 0.03 part by weight, particularly preferably 0.003 to 0.02 part by weight, based on 100 parts by weight of BS. If the quantity is less than 0.001 part by weight, the effectiveness of the inhibitor is little, while if it exceeds 0.05 part by weight, then when the composition of the present invention is used for polymerization, the resulting polymer may color, that is, such is undesirable.

In addition, the composition of the present invention is prepared by mixing BS, the aromatic vinyl compound and the polymerization inhibitor in an optional order. For example, the aromatic vinyl compound in a definite quantity may be mixed in a composition consisting of BS and the polymerization inhibitor, and it does not matter if the above mixing is reversed.

In the present invention, a monomer copolymerizable with the aromatic vinyl compound, an organic solvent, etc. may be further contained or mixed, and such substances are chosen taking into account conditions under which they are subjected to polymerization. As the monomer copolymerizable with the aromatic vinyl compound, those which are usually used for styrene polymerization such as vinyl monomers e.g. acrylonitrile, methyl methacrylate, etc. may be used alone or in admixture, and as to the proportion of such monomer, its quantity is less than the total quantity of the aromatic vinyl compound. Further, as the organic solvent, those which are usually used for styrene polymerization may be used, such as toluene, ethylbenzene, methyl ethyl ketone, dimethylformamide, etc., and its quantity is determined taking into account the polymerization conditions of the BS-containing composition. Usually, the more the quantity of the solvent, the better the storage stability, but since it is generally necessary to separate the solvent from the resulting polymer after polymerization, it is preferred to use the solvent in a proportion of ½ or less of the quantity of the total monomers.

The composition of the present invention can be usually stored or transported at room temperature, and also has a storage stability for two days or longer even at 45° C.

In order to improve the storage stability, it is preferred to put the composition of the present invention at a cold place and also put it in contact with air. In addition, to but it in contact with air may be attained by contacting the upper surface of the composition with air, but it does not matter if air is passed through the composition.

In addition, the storage stability of the composition in the present invention can be judged by introducing the BS composition before allowing it to stand and that after allowing it to stand, respectively into methanol in a quantity of 30 times that of the composition and measuring the quantities of the respective resulting precipitates.

The present invention will be further described in more detail by way of Examples. In addition, the BSs used in Examples and Comparative examples have compositions shown in Table 1.

TABLE 1

| BS composition (% by weight) | | | |
|---|---|---|---|
| Name of compound | BS1 | BS2 | BS3 |
| 4-Bromostyrene | 60 | 6 | 26 |
| 2-Bromostyrene | 35 | 3 | 57 |
| 2,4-Dibromostyrene | 5 | 81 | 15 |
| Tribromostyrene | — | 10 | 2 |

Further, the stability of the composition was evaluated according to the following method:

A composition to be tested, after allowed to stand under definite conditions, is introduced into methanol in a quantity of 30 times that of the composition with stirring, followed by filtering and drying the resulting precipitate. The quantity of the composition introduced into methanol is made $X_{BS}$ gr. and the quantity of the resulting precipitate is made $X_P$ gr. From these values is sought $X_P/X_{BS}$. From this value is evaluated the stability of the composition at the time of being allowed to stand. It is possible to judge that the smaller this value, the higher the stability. In addition, in the following Examples and Comparative examples, the values of the respective compositions before they were allowed to stand were all zero.

EXAMPLE 1~3

The respective compositions (each 10 ml) consisting of BS1, BS2 or BS3 as BS (each 100 parts by weight), styrene (100 parts by weight) and PTBC (0.01 part by weight) were placed in a 50 ml capacity beaker, and then allowed to stand at 45° C. for 2 days while the upper surface of the compositions was in contact with air. Thereafter the stabilities of the compositions were evaluated. The results are shown in Table 2.

COMPARATIVE EXAMPLES 1~3

Examples 1~3 were repeated except that no styrene was used, followed by evaluating the respective stabilities. The results are shown in Table 2.

COMPARATIVE EXAMPLE 4

Example 1 was repeated except that no PTBC was used, followed by evaluating the stability. The results are shown in Table 2.

EXAMPLE 4

Example 1 was repeated except that styrene was replaced by p-methylstyrene (100 parts by weight), followed by evaluating the stability. The results are shown in Table 2.

EXAMPLE 5

Example 3 was repeated except that PTBC was replaced by MQ (0.01 part by weight), followed by evaluating the stability. The results are shown in Table 2.

REFERENCE EXAMPLES 1, 2 and 3

For reference, a composition consisting of styrene (100 parts by weight) and PTBC (0.01 part by weight) was allowed to stand at 45° C. for 2 days (Reference example 1), a composition consisting of BS1 (100 parts by weight) and PTBC (0.01 part by weight) was allowed to stand at −20° C. for 2 days (Reference example 2), and a composition consisting of BS1 (100 parts by weight) ad PTBC (0.1 part by weight) was allowed to stand at 45° C. for 2 days (Reference example 3), followed by evaluating the respective stabilities. The results are also shown in Table 2.

EXAMPLE 6 AND COMPARATIVE EXAMPLE 5

The composition used in Example 1 and that used in Comparative example 1 were respectively placed in a glass ampoule having an inner diameter of 8 mm and a length of 25 cm so as to give an upper space of 15 cm, followed by bubbling nitrogen gas therethrough, replacing the atmosphere of the upper space by nitrogen gas, heat-sealing the ampoules, and then allowing them to stand at 45° C. for 2 days. The respective stabilities were then evaluated. The results are shown in Table 2.

TABLE 2

| | Composition (part by weight) | | | | | | | Storage conditions | | | Stability % |
|---|---|---|---|---|---|---|---|---|---|---|---|
| | BS*1 | | | Aromatic vinyl compound | | Polymerization inhibitor | | Atmo-sphere | Tempera-ture °C. | Number of days | |
| | BS1 | BS2 | BS3 | Styrene | PMS*2 | PTBC*3 | MQ*4 | | | | |
| Reference ex. 1 | — | — | — | 100 | — | 0.01 | — | air | 45 | 2 | <0.01 |
| Example 1 | 100 | — | — | " | — | " | — | " | " | " | <0.01 |
| Example 2 | — | 100 | — | " | — | " | — | " | " | " | <0.01 |
| Example 3 | — | — | 100 | " | — | " | — | " | " | " | <0.01 |
| Comparative ex. 1 | 100 | — | — | — | — | " | — | " | " | " | 0.7 |
| Comparative ex. 2 | — | 100 | — | — | — | " | — | " | " | " | 0.2 |
| Comparative ex. 3 | — | — | 100 | — | — | " | — | " | " | " | 0.4 |
| Compara- | 100 | — | — | 100 | — | — | — | " | " | " | 0.2 |

TABLE 2-continued

| | Composition (part by weight) | | | | | | Storage conditions | | | Stability % |
|---|---|---|---|---|---|---|---|---|---|---|
| | BS*1 | | | Aromatic vinyl compound | | Polymerization inhibitor | | Atmo-sphere | Tempera-ture °C. | Number of days | |
| | BS1 | BS2 | BS3 | Styrene | PMS*2 | PTBC*3 | MQ*4 | | | | |
| tive ex. 4 | | | | | | | | | | | |
| Example 4 | 100 | — | — | — | 100 | 0.01 | — | " | " | " | <0.01 |
| Example 5 | — | — | 100 | 100 | — | — | 0.01 | " | " | " | <0.01 |
| Reference ex. 2 | 100 | — | — | — | — | 0.01 | — | " | −20 | " | 0.01 |
| Reference ex. 3 | 100 | — | — | — | — | 0.1 | — | " | 45 | " | <0.01 |
| Example 6 | 100 | — | — | 100 | — | 0.01 | — | nitro-gen | " | " | 0.02 |
| Compara-tive ex. 5 | 100 | — | — | — | — | " | — | nitro-gen | " | " | 1.1 |

*1Mixture of bromostyrene with dibromostyrene (see Table 1)
*2Para-methylstyrene
*3Para-tertiary-butylcatechol
*4Hydroquinone monomethyl ether

EXAMPLES 7 AND 8

Example 1 was repeated except that the quantity of styrene used was varied to 25 parts by weight and 400 parts by weight, followed by evaluating the stabilities. The results are shown in Table 3.

EXAMPLE 9

Example 1 was repeated except that the quantity of PTBC used was reduced down to 0.002 part by weight, followed by evaluating the stability. The results are shown in Table 3.

EXAMPLE 10

Example 9 was repeated except that ethylbenzene (50 parts by weight) was further added to the composition of Example 9, followed by evaluating the stability. The results are shown in Table 3.

EXAMPLES 11 AND 12

Example 1 was repeated except that the quantity of PTBC used was reduced down to 0.005 part by weight, MQ (0.005 part by weight) was added and methyl methacrylate or acrylonitrile (each 20 parts by weight) was added, followed by evaluating the stabilities. The results are shown in Table 3.

EXAMPLE 13 AND COMPARATIVE EXAMPLE 6

The compositions of Example 1 and Comparative example 1 were respectively still stood at 20° C. for 30 days, followed by evaluating the stabilities. The results are shown in Table 3.

TABLE 3

| | Composition (part by weight) | | | | Additive | | Storage conditions | | | Stability % |
|---|---|---|---|---|---|---|---|---|---|---|
| | | | Polymerization inhibitor | | | | | Tempera- | Number | |
| | BS1*1 | Styrene | PTBC*3 | MQ*4 | Com-pound | Added quantity | Atmo-sphere | ture °C. | of days | |
| Example 1 | 100 | 100 | 0.01 | — | — | — | air | 45 | 2 | <0.01 |
| Example 7 | " | 25 | " | — | — | — | " | " | " | 0.05 |
| Example 8 | " | 400 | " | — | — | — | " | " | " | <0.01 |
| Example 9 | " | 100 | 0.002 | — | — | — | " | " | " | 0.03 |
| Example 10 | " | " | " | — | Ethyl-benzene | 50 | " | " | " | 0.03 |
| Example 11 | " | " | 0.005 | 0.005 | Methyl metha-crylate | 20 | " | " | " | 0.01 |
| Example 12 | " | " | " | " | Acrylo-nitrile | 20 | " | " | " | 0.01 |
| Example 13 | " | " | 0.01 | — | — | — | " | 20 | 30 | <0.01 |
| Compara-tive ex. 6 | " | — | " | — | — | — | " | " | " | 1.1 |
| Compara-tive ex. 1 | " | — | " | — | — | — | " | 45 | 2 | 0.7 |

*1See Table 1.
*3,4See footnotes of Table 2.

As seen in Tables 2 and 3, the composition of the present invention is superior in stability so that at 45° C. or lower, it is stable and storable over 2 days or longer. Further, since it contains an aromatic vinyl compound, it can be used directly as a new material for BS-modified polymers such as aromatic vinyl compound-containing polymers e.g. HIPS resin, AS resin, ABS resin, MBS resin, etc.; hence its commercially available value is great.

What we claim is:

1. A process for the stabilization of bromostyrene which comprises providing a bromostyrene composition comprising 100 parts by weight of bromostyrene having one, two or three bromine atoms substituted on the nucleus thereof and 0.001 to 0.05 parts by weight of a polymerization inhibitor and adding 20 to 3,000 parts by weight of an aromatic vinyl compound to said bromostyrene composition.

2. A process of claim 1 wherein said aromatic vinyl compound is at least one member selected from the group consisting of styrene, substituted styrenes and vinylnaphthalene.

3. A process of claim 1 wherein said bromostyrene composition contains a vinyl monomer copolymerizable with said aromatic vinyl compound.

4. A process of claim 1 wherein said bromostyrene composition contains an organic solvent.

* * * * *